(12) United States Patent
Embaye et al.

(10) Patent No.: US 8,244,477 B1
(45) Date of Patent: Aug. 14, 2012

(54) ESTIMATION OF ALGA GROWTH STAGE AND LIPID CONTENT GROWTH RATE

(75) Inventors: Tsegereda N. Embaye, Boulder Creek, CA (US); Jonathan D. Trent, La Selva Beach, CA (US)

(73) Assignees: The United States of America as represented by the Administrator of the National Aeronautics and Space Administration (NASA), Washington, DC (US); SETI Institute, Mountain View, CA (US)

( * ) Notice: Subject to any disclaimer, the term of this patent is extended or adjusted under 35 U.S.C. 154(b) by 506 days.

(21) Appl. No.: 12/478,667

(22) Filed: Jun. 4, 2009

(51) Int. Cl.
*G01N 33/48* (2006.01)
*G01N 31/00* (2006.01)

(52) U.S. Cl. .......................................... 702/19; 702/23

(58) Field of Classification Search .................. None
See application file for complete search history.

(56) References Cited

U.S. PATENT DOCUMENTS

| | | | |
|---|---|---|---|
| 7,118,700 | B2 | 10/2006 | Eisner |
| 2009/0029445 | A1 | 1/2009 | Eckelberry et al. |
| 2009/0130747 | A1 | 5/2009 | Wen-Teng et al. |

OTHER PUBLICATIONS

Levert et al. "Modeling the growht curve for *Spirulina* (*Arthrospira*) maxima, a versatile microalga for producing uniformly labelled compounds with stable isotopes," J. of Applied hycology, vol. 13 (2001) p. 359-367.*

Benson et al. "The development of a mechanistic model to investigate the impacts of the light dynamics on algal prodoctivity in a Hydraulically Integrated Serial Turbiodostat Algal Reactor (HISTAR)," Aquacultura Engineering, vol. 36 (2007) p. 198-211.*

Lee, Oceanographic Instruments Monitor Fishpond Algae, Agricultural Research, Nov. 1996, 24, 44-11, http://www.ars.usda.gov/is/AR/archive/nov96/.

Steitz, et al., NASA Technology Tracks Consequences of Hurricane Floyd, NASA Headquarters News, Nov. 2, 1999, Release: 99-126, http://www.nasa.gov/home/hqnews/1999/99-126.txt.

* cited by examiner

*Primary Examiner* — Marjorie Moran
*Assistant Examiner* — Anna Skibinsky
(74) *Attorney, Agent, or Firm* — John F. Schipper; Robert M. Padilla (57) ABSTRACT

Method and system for estimating a growth stage of an alga in an ambient fluid. Measured light beam absorption or reflection values through or from the alga and through an ambient fluid, in each of two or more wavelength sub-ranges, are compared with reference light beam absorption values for corresponding wavelength sub-ranges for in each alga growth stage to determine (1) which alga growth stage, if any, is more likely and (2) whether estimated lipid content of the alga is increasing or has peaked. Alga growth is preferably terminated when lipid content has approximately reached a maximum value.

16 Claims, 11 Drawing Sheets

ESTIMATION OF ALGA GROWTH STAGE AND LIPID CONTENT GROWTH RATE

ORIGIN OF THE INVENTION

This invention described herein was made in the performance of work under a NASA contract and by an employee of the United States Government and is subject to the provisions of Public Law 96-517 (35 U.S.C. §202) and maybe manufactured and used by or for the Government for governmental purposes without the payment of any royalties thereon or therefore.

FIELD OF THE INVENTION

This invention relates to methods of estimation of alga growth stage and lipid content growth rate for alga in marine water, in fresh water and in any other fluid, using light absorption or light reflection (collectively referred to as "light modification") in selected wavelength ranges.

BACKGROUND OF THE INVENTION

In many approaches to production of fuels, nutraceuticals and other useful products by growth and conversion of algae products, a growth stage of alga in a controlled environment must be evaluated, for purposes of estimation of lipid contant and for other metrics. It is often very inaccurate to estimate alga growth stage based only on time of growth, because of variations in important environmental parameters during different growth cycles.

What is needed is a more accurate approach that does not depend solely on time of growth and that implicitly factors in the variable environmental parameters and provides a useful error estimate for alga growth stage. Preferably, the approach should implicitly or explicitly take account of the environmental history of growth of the alga.

SUMMARY OF THE INVENTION

These needs are met by the invention, which provides a method using selective modification of light in different wavelength ranges to estimate (i) alga growth stage and (ii) alga growth rate in an ambient fluid (e.g., air, vacuum, fresh water, marine water and/or brine). In a first embodiment, absorption of light is measured for a beam, having a specified light intensity in each of two or more specified narrow wavelength ranges of light, $\lambda 1_n \leq \lambda \leq \lambda 2_n$. (n=1, 2, ..., N; N≧3). Optionally, light absorption is compensated for absorption of light in the same wavelength range by the ambient medium (vacuum or a specified fluid). The net absorption of light in N wavelength ranges (N≧3) is compared with a reference set of net absorption values for the alga for different growth stages. An algorithm is applied to differences between measured net absorption values and reference net absorption values to estimate a growth stage (one of a discrete sequence of growth stages). Compensation for light reflection from a liquid (absent alga) is similar.

In a second embodiment, lipid content of the alga is measured or estimated at each of a selected set of growth stages. In some algae, the lipid content increases to a maximum, and the lipid content thereafter reaches a plateau. In some other algae, the lipid content increases to a maximum and thereafter decreases to a lower value, indicating that the alga growth process should be terminated at some time in order to accumulate the largest lipid content from that alga.

In a third embodiment, the estimated growth stage is correlated with a time variable, t−t0, where t0 is an estimated time for initiation of growth the alga under specified conditions. A temporal rate of alga growth from one stage to the next stage is estimated, and this rate is correlated with accumulated time, t−t0, to allow an estimate of sensitivity of accumulated lipid content with a time for cut-off of alga growth.

In a fourth embodiment, one or more relevant environmental parameters (light intensity, light wavelength, temperature, iron content, etc.) is varied for the alga, and a time Δt(hours) required for the algae to progress from an initial stage to a specified "end stage" is determined, based on variation of the parameters one at a time. The inverse 1/Δt(hours) is taken to represent an average growth rate of the algae. A particular combination of environmental parameter values is identified for which the average growth rate is greatest (1/Δt(hours) is smallest).

DESCRIPTION OF BEST MODES OF THE INVENTION

Figure 1:
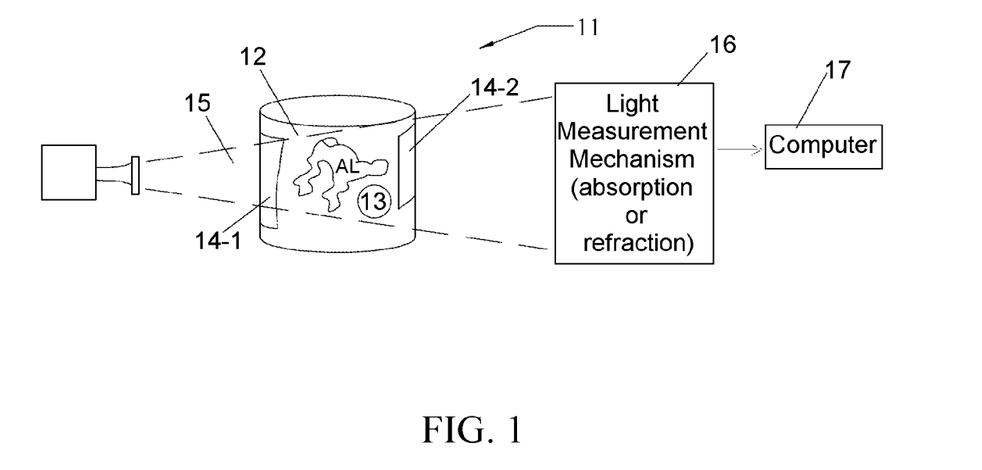
FIG. 1 schematically illustrates an experimental set-up for practicing an embodiment of the invention.

FIG. 1 schematically illustrates a system 11 for practicing the invention. A specified alga AL is suspended in a chamber 12 in an ambient fluid medium 13 (vacuum, air, fresh water, marine water, a specified gas or vapor at a specified pressure, etc.), where the chamber 12 has first and second windows (or, optionally, a single wraparound window), 14-1 and 14-2, that face each other and that are substantially transparent throughout a range of wavelengths, λ(lower)≦λ≦λ(upper), that includes the wavelengths of interest. A light beam 15, preferably filtered to transmit light in only one of a sequence of N wavelength ranges, $\lambda 1_n \leq \lambda \leq \lambda 2_n$. (n=1, ..., N; N≧3), illuminates the alga AL through the first widow 14-1. Light not modified by the alga and not absorbed (or reflected) by the ambient medium within the chamber 12 passes through the second window 14-2, or a second portion of the first window, and modified light is received by a light measurement mechanism 16, which sequentially or simultaneously measures light intensity I(n) received in the wavelength ranges $\lambda 1_n \leq \lambda \leq \lambda 2_n$. (n=1, ..., N; N≧3)

A computer 17 associated with the light measurement mechanism 16 receives the measured (modified) light intensity value I(n) for each of N wavelength ranges, $\lambda 1_n \leq \lambda \leq \lambda 2_n$, and estimates light modification in each wavelength range of interest. Optionally, the computer 17 applies a procedure to compensate for light intensity modified by the ambient medium (with alga absent) and by the window material in each wavelength range of interest, $\lambda 1_n \leq \lambda \leq \lambda 2_n$.

For example, if a simple Beers' law exponential absorption model is applied, the total light absorption is a sum of the exponential absorption factors, α(alga;n) and α(ambient;n) and α(window;n), for the alga and for the ambient medium and window(s), respectively; and the net alga transmission is then expressible as $$I(\text{net};n) = I_0(n)\exp\{\alpha(\text{ambient};n) + \alpha(\text{window};n)\}\exp\{-\alpha(\text{alga};n)\}, \quad (1)$$

with $\alpha(\text{alga};n)$ replaced by $\alpha(\text{alga refl};n)$ for light reflection in Eq. (1). The factor $\exp\{\alpha(\text{ambient};n) + \alpha(\text{window};n)\}$ is estimated in a separate experiment and is made available as a reference value for different algae. The computer 17 computes the net transmission $I(\text{net};n)^*$ and estimates net alga modification in the wavelength range, $\lambda 1_n \leq \lambda \leq \lambda 2_n$. Optionally, the computer 17 can estimate a volume or opaqueness factor for the alga (displacement of fluid by the alga) within the chamber and can further modify the alga modification factor $\alpha(\text{alga};n)$ to account for absence of the ambient fluid wherever the alga is present.

A suitable wavelength range width for measurement of alga absorption may be $\lambda 2_n - \lambda 1_n = 5-50$ nm, depending upon the average wavelength, $\{\lambda 2_n + \lambda 1_n\}//2$. Where the absorption factor $\alpha(\text{alga};n)$ is changing rapidly with the index n, the wavelength range width should be smaller; use of non-uniform widths is preferred here.

A sequence of net absorption values $\{\alpha(\text{alga};n)\}_n$ for each of the wavelength ranges of interest is compared with a reference set of values $\{\alpha(\text{ref};n;\text{alga growth stage } g)\}_n$ to estimate an error, between reference value and measured value, for each of G stages of growth, numbered $g=1, \ldots, G$ ($G \geq 2$). FIGS. 3-8 illustrate a representative group of N net light modification values (N=3) for different growth stages of an alga, *Chlorella vulgaris*, *Chlorella* (mixed species) and *Scenedesmus*.

One estimate of the associated error is $$\varepsilon(g) = \sum_{n=1}^{N} w_n |\alpha(\text{net};n) - \alpha(\text{ref};n;\text{growth stage } g)|^p (g=1, \ldots, G), \quad (2)$$

where $\{w_n\}_n$ is a sequence of selected non-negative weight values and p is a selected positive number, for example, p=1, p=2 or p=selected rational or irrational number. The growth stage error values $\varepsilon(g)$ are compared with each other and with a threshold error value $\varepsilon(\text{thr})$. Where a particular growth stage error value, $\varepsilon(g=g0)$, satisfies the conditions $$\varepsilon(g0) = \min\{\varepsilon(g=1), \ldots, \varepsilon(g=G)\}, \quad (3A)$$

$$\varepsilon(g0) \leq \varepsilon(\text{thr}), \quad (3B)$$

this is interpreted as indicating that the alga growth stage $g=g0$ is the most likely growth stage, based on the N measurements of alga net absorption.

Figure 2A:
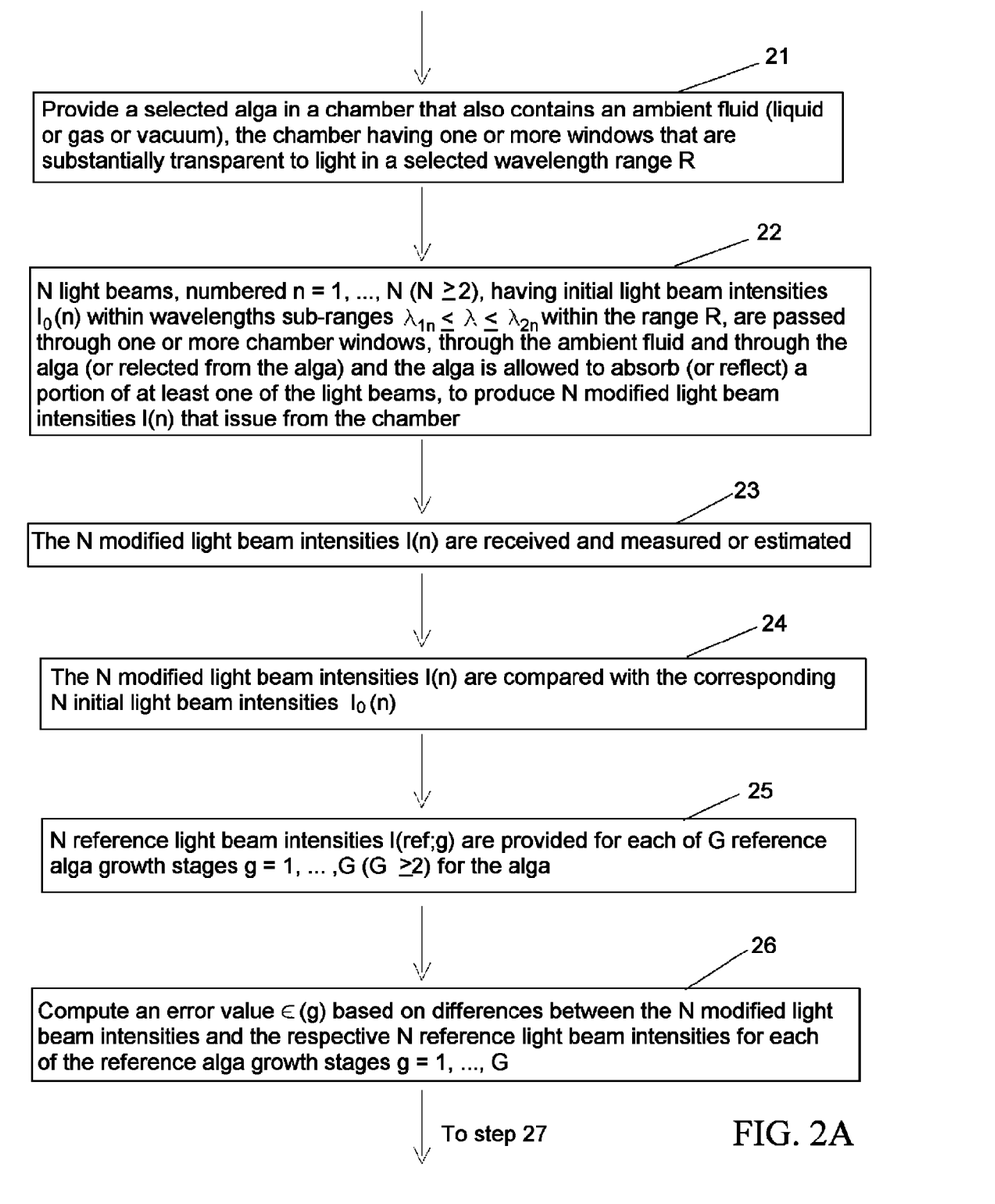
FIG. 2 is a flow chart of a procedure for practicing the invention.
Figure 2B:
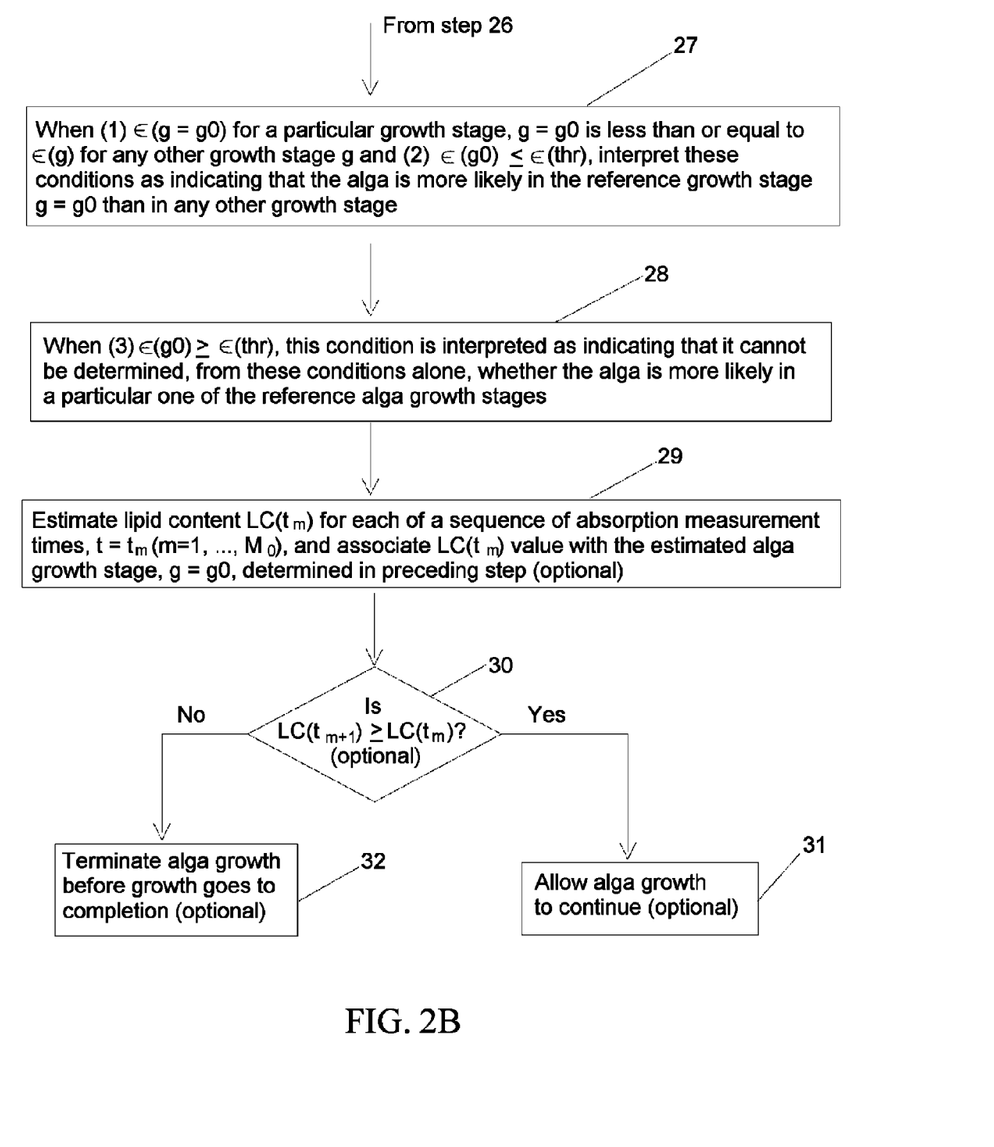

FIG. 2 is a flow chart of a procedure for practicing an embodiment of the invention. In step 21, an alga, having a growth stage that may be unknown, is placed in a chamber that also contains an ambient fluid (liquid or gas or vacuum), the chamber having one or more windows that are substantially transparent to light in a selected wavelength range R.

In step 22, N light beams, having initial light beam intensities $I_0(n)$ (n=1, ..., N; $N \geq 2$) within the wavelength subranges, respectively, within the range R, are passed through the one or more chamber windows, through the ambient fluid and through the alga, and at least one of the ambient fluid and the alga is allowed to absorb a portion of at least one of the N light beams, to produce N modified light beam intensities I(n) that issue from the chamber.

In step 23, the N modified light beam intensities are received and measured or estimated.

In step 24, the N modified light beam intensities I(n) are compared with the corresponding N initial light beam intensities $I_0(n)$ In step 25, N reference light beam intensities I(ref;n;g) are provided for the N wavelength ranges for each reference growth stage g (g=1, ..., G; $G \geq 2$).

In step 26, an error value $\varepsilon(g)$ is computed, based upon differences between the N modified light beam intensities and the corresponding N reference light beam intensities for each of the reference alga growth stages, g=1, ..., G, When (1) the error value $\varepsilon(g=g0)$ for a particular growth stage, g=g0, is less than or equal to the error value $\varepsilon(g)$ for any other value of g and (2) the error value $\varepsilon(g0)$ is no greater than a selected threshold error value $\varepsilon(\text{thr})$, these conditions are interpreted, in step 27, as indicating that the alga is more likely in the reference growth stage g=g0 than in any other reference growth stage.

When (3) the error value $\varepsilon(g0)$ is greater than the selected threshold error value $\varepsilon(\text{thr})$, these conditions are interpreted, in step 28, as indicating that it cannot be determined, from these conditions alone, whether the alga is more likely in a particular one of the reference alga growth stages.

In step 29 (optional), the lipid content $LC(t_m)$ of the alga is estimated for each of a sequence of absorption measurement times, $t=t_m$ (m=1, ..., $M_0$), and the estimated value $LC(t_m)$ is associated with the estimated alga growth stage, g=g0, determined in the preceding step. In step 30 (optional), the system determines whether the estimated lipid content $LC(t_m)$ increases (strictly), expressed as $LC(t_{m+1}) \geq LC(t_m)$. Where the answer to the query in step 30 is "yes," the system interprets this response as indicating that the estimated lipid content does not (yet) decrease with increasing time, $t=t_m$, and alga growth is allowed to continue, in step 31 (optional).

Where the answer to the query in step 30 is "no" so that the estimated lipid content is no longer increasing (strictly) monotonically, the system interprets this response as indicating that estimated lipid content may decrease with time beyond a certain growth stage. One consequence of this last interpretation is that alga growth should be terminated, in step 32 (optional), before growth continues, in order to maximize lipid content that may be extracted from the alga.

Certain algae, when fully grown, have a relatively high lipid content and can be used as a feedstock for extraction of biofuels, diesel fuels, nutraceuticals, pharmaceuticals, fertilizer, animal feed and other useful products. Algae to which the invention has been applied to evaluate alga growth stage and alga lipid content include *Chlorella vulgaris*, *Chlorella* (mix) and *Scenedusmus*.

Figure 3:
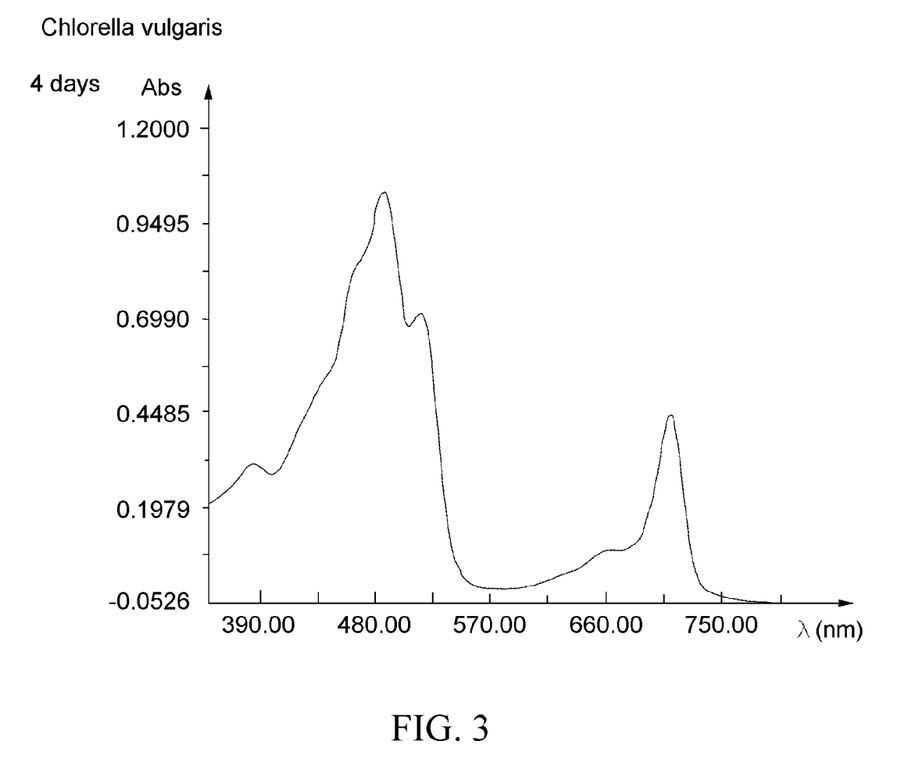
FIGS. 3-8 are graphical illustrations of alga absorption versus wavelength for selected algae.
Figure 4:
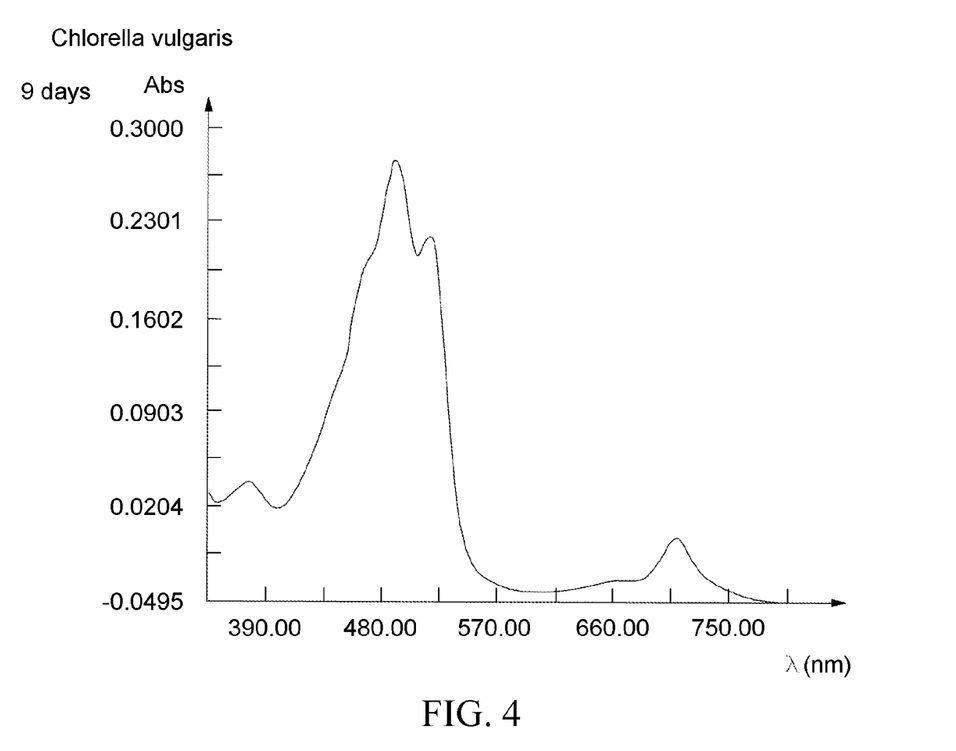

FIGS. 3 and 4 are graphical illustrations of measured absorption $\alpha(\text{alga};n)$ in *Chlorella vulgaris* versus wavelength $\lambda$(nm) for a wavelength range of about 300 nm $\leq \lambda \leq$ 750 nm at four days growth (FIG. 3) and at nine days growth (FIG. 4). The following differences are observed between FIGS. 3 and 4: (1) a local maximum in absorption value at $\lambda \approx 370$ nm for four days growth is larger than the corresponding peak for nine days growth; (2) a local minimum in absorption at $\lambda \approx 390$ nm for four days growth has a larger value than the corresponding absorption minimum value for nine days growth; (3) the maximum absorption value (at $\lambda \approx 400$ nm) for nine days growth is larger than the corresponding absorption peak for four days growth; (4) a local minimum absorption value (at $\lambda \approx 420$ nm) has a higher value for nine days growth than the corresponding local minimum absorption value for four days growth; (5) a local maximum absorption value (at $\lambda \approx 700$ nm) for four days growth has a higher value than the corresponding local maximum absorption value for nine days growth.

Figure 5:
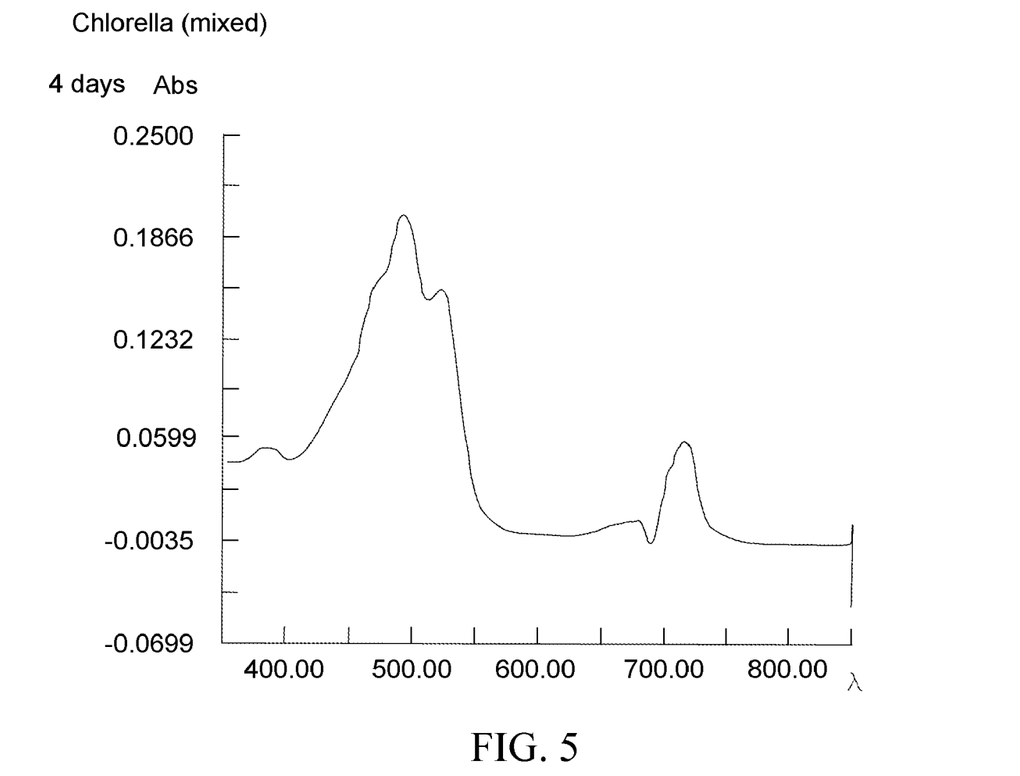
Figure 6:
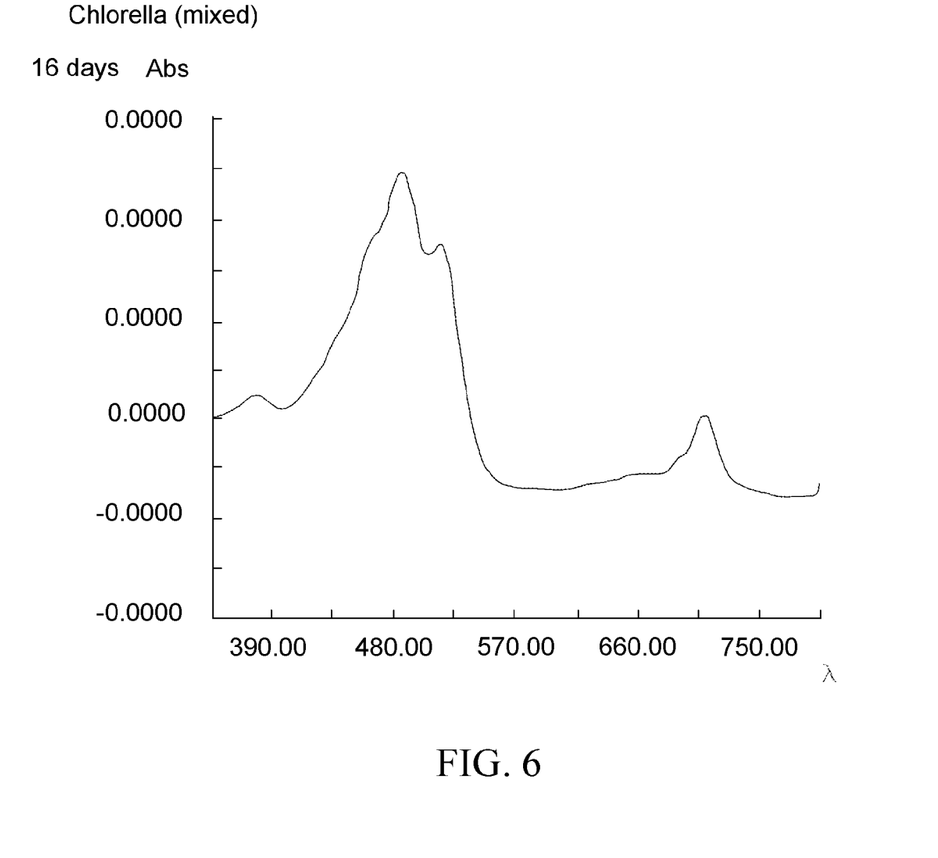

FIGS. 5 and 6 are graphical illustrations of measured absorption α(alga;n) in *Chlorella* (mixed species) versus wavelength λ(nm) for a wavelength range of about 300 nm≦λ≦750 nm at growth stage four days growth (FIGS. 5) and 16 days growth (FIG. 6). The following differences are observed between FIGS. 5 and 6: (1) a local absorption maximum (at λ≈380 nm) for 16 days growth is more pronounced than the corresponding peak at four days growth; (2) a subsequent minimum absorption value (at λ=395 nm) for 16 days growth is larger than a corresponding minimum absorption value for four days growth; (3) the wavelength for the minimum value in (2) for 16 days growth is shifted relative to the wavelength for the corresponding minimum value for four days growth; (4) the maximum absorption peak (at λ≈470 nm) for 16 days growth is larger than the corresponding maximum absorption peak for four days growth; (5) a subsequent local absorption maximum value (at λ≈520 nm) for 16 gays growth is larger than the corresponding peak for four days growth; (6) a local minimum value for absorption (at λ≈680 nm) for four days growth has disappeared at 16 days growth; and (7) a local maximum absorption peak (at λ≈710 nm) for four days growth is larger than the corresponding local maximum absorption peak for 16 days growth.

Figure 7:
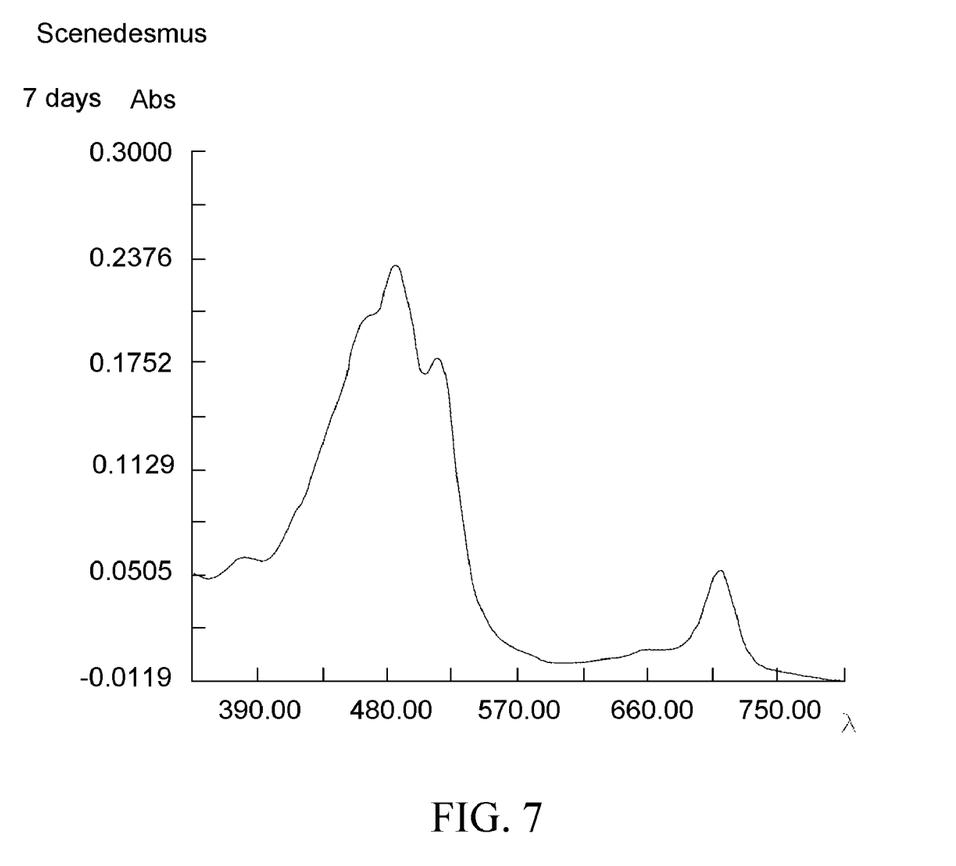
Figure 8:
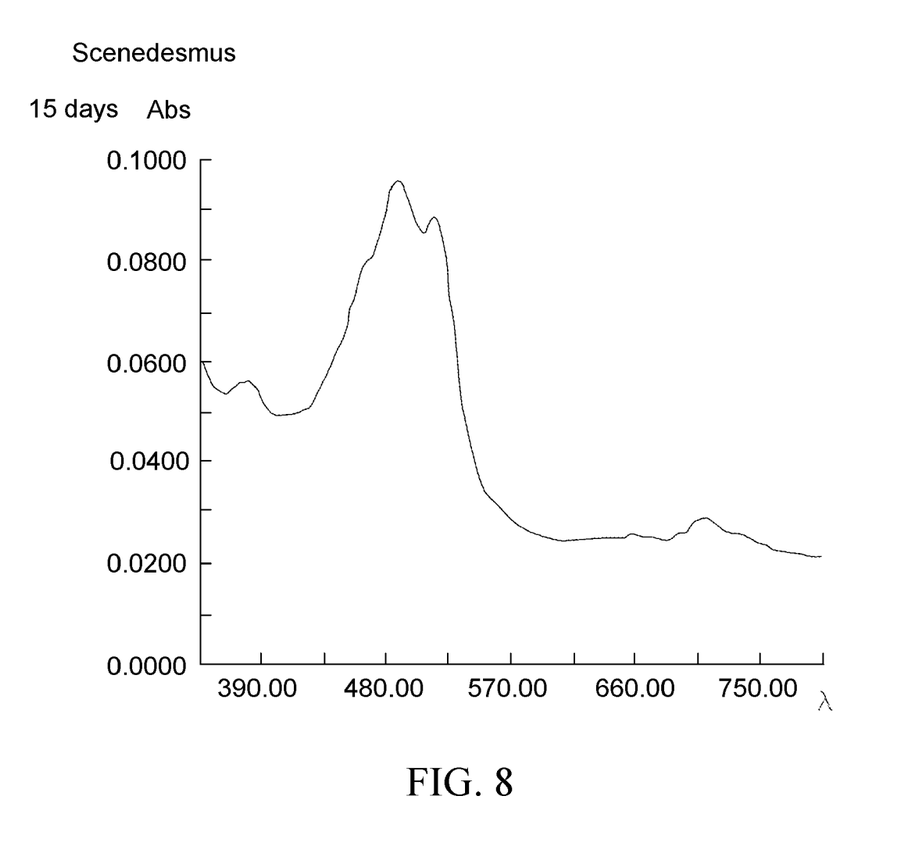

FIGS. 7 and 8 are graphical illustrations of measured absorption α(alga;n) in *Scenedesmus* versus wavelength λ(nm) for a wavelength range of about 300 nm≦λ≦750 nm at growth stage seven days growth (FIG. 7) and 15 days growth (FIG. 8). The following differences are observed between FIGS. 7 and 8: (1) a local maximum absorption value (at λ≈380 nm) for 15 days growth is larger than the corresponding local maximum value for seven days growth; (2) a local minimum absorption value (at λ≈395 nm) for 15 days growth is larger than the corresponding local minimum value for seven days growth; (3) the maximum absorption value (at λ≈480 nm) for 15 days growth is larger than the corresponding maximum absorption value for seven days growth; (4) a local minimum absorption value (at λ≈500 nm) for 15 days growth is larger than the corresponding minimum value for seven days growth; (5) a local maximum absorption value (at λ≈500 nm) for 15 days growth is larger than the corresponding maximum value for seven days growth; and (6) a local maximum absorption value (at λ≈690 nm) for seven days growth is larger than the corresponding maximum value for 15 days growth, where this local maximum value has nearly disappeared.

One or more of five factors contributes to absorption graph differences between two or more distinct alga growth stages: (i) differences in (local or absolute) absorption maximum values; (ii) differences in wavelength value for the (local or absolute) absorption maximum values; (iii) differences in local absorption minimum values; (iv) differences in wavelength value for the local absorption minimum values; and (v) appearance of a prominent feature (e.g., maximum or minimum absorption value) at one growth stage that is absent at another growth stage. Reflection graph differences between two alga growth stages arise from: (i) appearance or disappearance of a prominent reflection feature at a growth stage and (ii) reflectivity differences at different growth stages.

Figure 9:
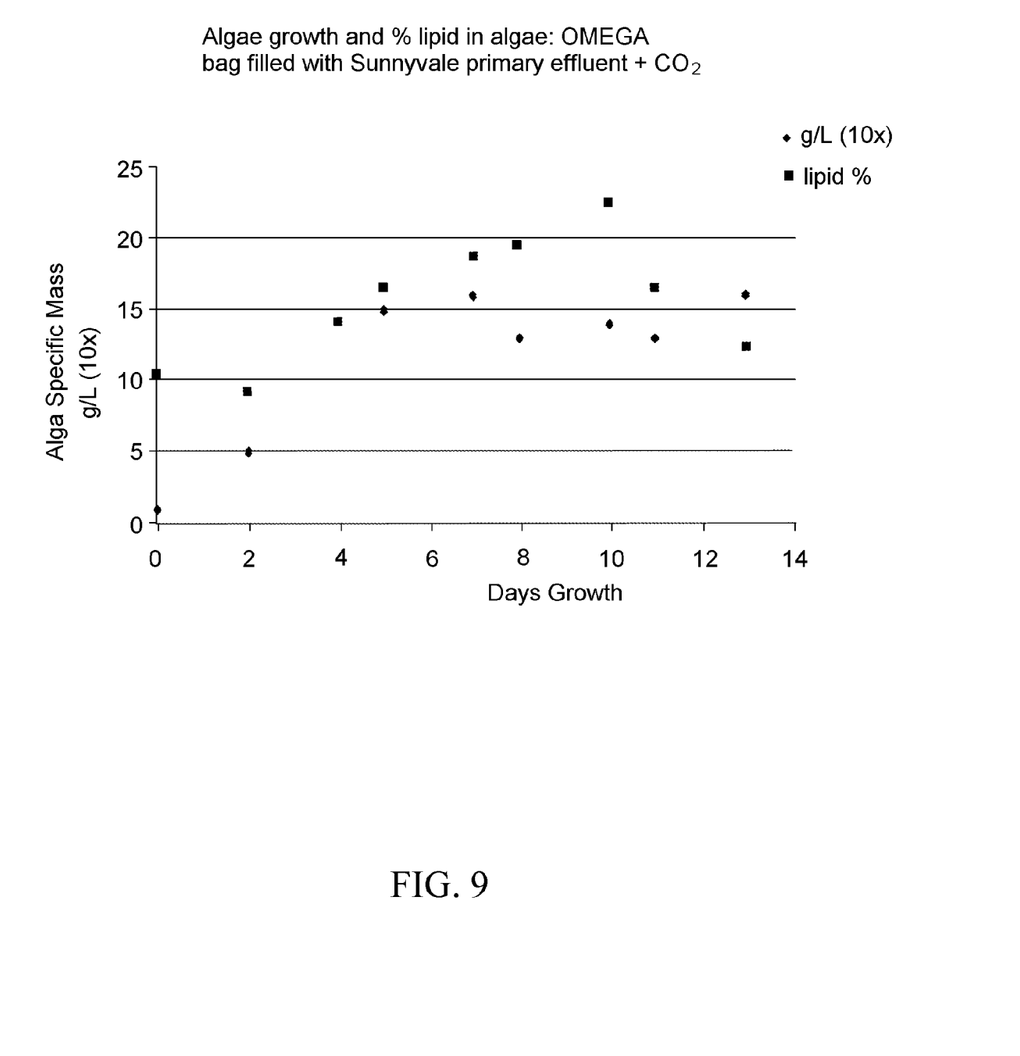
FIGS. 9-10 are graphical illustrations comparing alga specitic mass and alga lipid content versus alga growth time.
Figure 10:
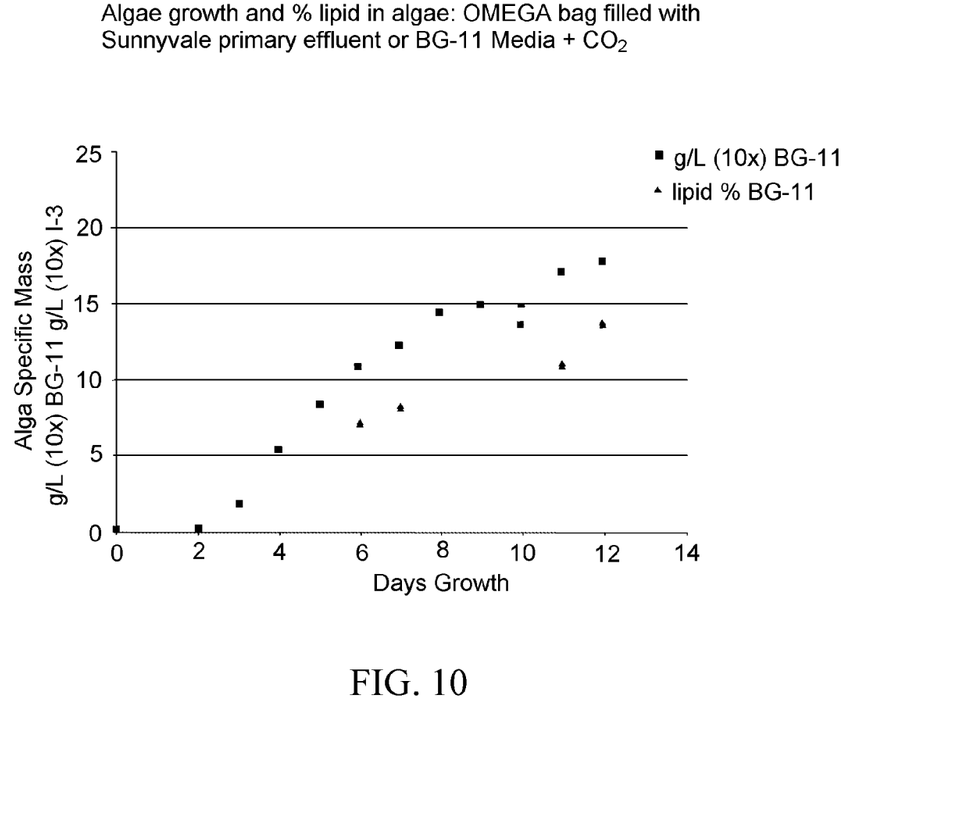

FIGS. 9 and 10 graphically illustrate alga mass (gms/liter) and percent lipid content for *Chlorella vulgaris*, for a bag filled with City of Sunnyvale primary effluent plus $CO_2$ (FIG. 9) and for a bag filled with BG-11 media plus $CO_2$ (FIG. 10), versus number of days of alga growth (1-14). With reference to FIG. 9, the alga specific mass increases to a value of about 15 gm/liter at about seven days growth and thereafter plateaus or decreases slightly, while lipid content of the alga continues to increase to about 22 percent at about ten days growth, and thereafter decreases sharply and plateaus at a lower value of about 12 percent on day 14. These responses indicate that, for *Chlorella vulgaris*, in the Sunnyvale effluent, the alga should be harvested shortly after the alga first achieves maximum growth, in order to obtain maximum lipid content.

With reference to FIG. 10, the alga specific mass increases through day 12; the lipid percent increases until day 10 and decreases sharply beyond day 10, when the alga specific mass is still increasing. These responses indicate that, for *Chlorella vulgaris*, in the BG-11 media, the alga should be harvested before or shortly after the alga first achieves maximum growth, in order to obtain maximum lipid content. Delaying the harvest beyond about nine or ten days growth will result in reduced total lipid content. The differences inn the lipid content response in FIGS. 9 and 10 indicate that lipid growth may depend upon the particular alga and upon the alga growth medium, From FIGS. 9 and 10, one notes that the rate of alga growth varies substantially with its present "age," and accurate prediction of ultimate (saturated) specific mass of the alga is probably not possible. However, one can estimate a present rate of alga growth, using two or three rates at preceding times as a predictor. When the estimated present rate of growth is below a specified threshold (e.g., 2-4 gm/liter/day), one can conclude that alga growth saturation is near and treat the current state of the alga as an end state.

Estimated lipid content associated with the alga growth at an alga harvest time can also be optimized by the following procedure. The rate of alga growth at each of the sequence of measurement times, $t=t_m$, is estimated as follows. For three measurement times, $t=t_{m-1}$, $t_m$, and $t_{m+1}$, with $t_{m-1} < t_1 < t_{m+1}$ the quadratic function $$Q(t; t_{m-1}, t_m, t_{m+1}) = LC(t_{m-1})(t-t_m)(t-t_{m+1})/(t_{m-1}-t_m) \\ (t_{m-1}-t_{m+1}) + LC(t_m)(t-t_{m-1})(t-t_{m+1})/(t_m-t_{m-1}) \\ (t_m-t_{m+1}) + LC(t_{m+1})(t-t_{m-1})(t-t_m)/(t_{m-1}-t_{m-1}) \\ (t_{m+1}-t_m) \quad (4)$$

reproduces the lipid content values $LC(t_{m+x})$ ($x=-1, 0, +1$) at the respective time values $t=t_{m-x}$. The time derivative of $Q(t; t_{m-1}, t_m, t_{m+1})$ at the intermediate time value, $t=t_m$), is $$\{\partial Q/\partial t\}_{t=tm} = LC(t_{m-1})(t_m-t_{m+1})/(t_{m-1}-t_m)(t_{m-1}- \\ t_{m+1}) + LC(t_m)(2t_m-t_{m-1}-t_{m+1})/(t_m-t_{m-1})(t_m- \\ t_{m+1}) + LC(t_{m+1})(t-t_{m-1})/(t_m-t_{m-1})(t_{m+1}-t_m). \quad (5)$$

When the lipid content growth rate $\{\partial Q/\partial t\}_{t=tm}$ is negative, is zero, or is positive but small relative to preceding values of the lipid content growth rate, alga growth should be terminated and the alga (and associated lipid content) should be harvested, at a time contemporaneous with the alga termination time t(term). A computer can be programmed to compute the quantity $\{\partial Q/\partial t\}_{t=tm}$ at each of the measurement times, $t=t_m$, and to determine when to terminate alga growth.

What is claimed is:

1. A method for estimating a stage of growth of a selected algae, the method comprising:

placing an algae, having a growth stage that may be unknown, in a chamber that also contains an ambient fluid, the chamber having one or more windows that are at least partly transparent to light in a selected wavelength range R;

passing N light beams, numbered n=1, . . . , N (N≧2), having initial light beam intensities $I_0(n)$ and having wavelength sub-ranges $\lambda 1_n \leq \lambda \leq \lambda 2_n$, respectively, within the range R, through the one or more chamber windows, through the ambient fluid and through the algae, and allowing at least one of the ambient fluid, the one or more chamber windows and the algae to absorb a portion of at least one of the N light beams, to produce modified light beams, numbered n=1, . . . , N, in the respective wavelength sub-ranges, that have passed through the chamber;

receiving the modified N light beams and estimating or measuring modified light beam intensities, I(n), numbered n=1, . . . , N, for the respective N modified light beams;

providing N reference light beam intensities I(ref;n;g), numbered n=1, . . . , N, for each reference growth stage, numbered g=1, . . . , G (G≧2) for the selected algae;

comparing the N modified light beam intensities I(n) with the corresponding N reference initial light beam intensities I(ref;n;g) for each reference growth stage g of the algae;

computing an error value ϵ(g), based upon differences between the N modified light beam intensities I(n) and the respective N reference light beam intensities I(ref;n; g), for each growth stage g of the algae; and when, for a selected growth stage number g0, (1) the error value ϵ(g) for at least one growth stage, g–g0, is no greater than a value ϵ(g'), for any other growth stage g', and (2) ϵ(g0) is no greater than a selected error threshold value ϵ(thr), interpreting these conditions as indicating that the algae is most likely in the growth stage g0.

2. The method of claim 1, further comprising:
when, for said selected algae growth stage number g0, (3) ϵ(g) is greater than ϵ(thr) for said selected error threshold value, interpreting this condition as indicating that it cannot be determined, from this condition alone, whether said algae is most likely in said growth stage g0.

3. The method of claim 1, further comprising choosing at least one of said error value ϵ(g) to be expressed as $$\varepsilon(g) = \sum_{n=1}^{N} w_n |\alpha(n; net) - \alpha(ref; n; \text{growth stage } g)|^p,$$

where g refers to said growth stage of said algae, α(n;net) is a light beam absorption factor corresponding to said modified light beam intensity I(n), α(ref;n;growth stage g) is a reference light beam absorption factor corresponding to said reference light beam intensity I(ref;n;g) for said algae growth stage g, $w_n$ is a selected non-negative weight value, and p is a selected positive number.

4. The method of claim 1, further comprising choosing said ambient fluid to include at least one of air, a vacuum, fresh water and marine water.

5. The method of claim 1, further comprising:
providing an estimate LC(g') of lipid content in said algae at each of a sequence of growth stages g'=1, . . . , G';
estimating a growth stage, g'=g'(max) at which the lipid content LC(g') is maximized; and
when said most likely growth stage g0 has a value at least equal to g'(max), terminating a growth process for said algae.

6. The method of claim 1, further comprising:
providing an estimate LC of lipid content in said algae at each of a sequence of growth stages g', corresponding to times t=$t_{g'}$, (g'=1, . . . , G'; G'≧3};
estimating a time rate of change, ∂LC/∂t, of the lipid content LC for at least one selected time, t=$t_{g'}$, t=$t_{g'+1}$ and t=$t_{g'+2}$; and
when the estimated time rate of change of the lipid content for the selected time, t=$t_{g'}$, is either negative or 0 or has a small positive value, terminating growth of said algae at a time contemporaneous with the time t=$t_{g'}$.

7. The method of claim 6, wherein said process of estimating said time rate of change ∂LC/∂t comprises:
providing a sequence $\{LC(t_m)\}_m$ of measurements or estimates of lipid content of a selected alga at a sequence of times, t=$t_m$, and
for at least three measurement times, t=$t_{m-1}$, $t_m$, $t_{m+1}$, with $t_{m-1} < t_m < t_{m+1}$, estimating said lipid content growth rate at a time, t=$t_m$, as $$\{\partial Q/\partial t\}_{t=tm} = LC(t_{m-1}) (t_m - t_{m+1})/(t_{m-1} - t_m)(t_{m-1} - t_{m+1}) + LC(t_m)(2t_m - t_{m-1} - t_{m+1})/(t_m - t_{m-1})(t_m - t_{m+1}) + LC(t_{m+1})(t - t_{m-1})/(t_m - t_{m-1})(t_{m+1} - t_m).$$

8. The method of claim 1, wherein said process of providing N reference light beam intensities I(ref;n;g) for at least one of said algae growth stages g for said selected algae comprises
providing an exponential absorption value α(ambient;n) for a thickness of said ambient fluid in which said algae is immersed;
providing an exponential absorption value α(window;n) for said chamber window or chamber windows through which at least one of said light beams passes;
estimating an overall light beam attenuation as exp{–α(algae;n;g)}, and
estimating said reference light beam intensity by a relation I(net;n;g)=$I_0$(n) exp{α(ambient;n)+α(window;n)} exp{–α(algae;n)}.

9. A method for estimating a stage of growth of a selected algae, the method comprising:
placing an algae, having a growth stage that may be unknown, in a chamber that also contains an ambient fluid, the chamber having one or more windows that are at least partly transparent to light in a selected wavelength range R;
passing N light beams, numbered n=1, . . . , N (N≧2), having initial light beam intensities $I_0$(n) and having wavelength sub-ranges $\lambda 1_n \leq \lambda \leq \lambda 2_n$, respectively, within the range R, through the one or more chamber windows, through the ambient fluid, allowing the algae to reflect the light as a reflected light beam, and allowing at least one of the ambient fluid, the one or more chamber windows and the algae to reflect a portion of at least one of the N light beams, to produce modified light beams, numbered n=1, . . . , N, in the respective wavelength sub-ranges, that have been reflected;
receiving the modified N light beams and estimating or measuring modified light beam intensities, I(n), numbered n=1, . . . , N, for the respective N modified light beams;
providing N reference light beam intensities I(ref;n;g), numbered n=1, . . . , N, for each reference growth stage, numbered g=1, . . . , G (G≧2) for the selected algae;
comparing the N modified light beam intensities I(n) with the corresponding N reference initial light beam intensities I(ref;n;g) for each reference growth stage g of the alga;
computing an error value ϵ(g), based upon differences between the N modified light beam intensities I(n) and the respective N reference light beam intensities I(ref;n; g), for each growth stage g of the algae; and
when, for a selected growth stage number g0, (1) the error value ϵ(g) for at least one growth stage, g–g0, is no greater than a value ϵ(g'), for any other growth stage g', and (2) ϵ(g0) is no greater than a selected error threshold value ε(thr), interpreting these conditions as indicating that the algae is most likely in the growth stage g0.

10. The method of claim 9, further comprising:
when, for said selected growth stage number g0, (3) ε(g) is greater than ε(thr) for said selected error threshold value, interpreting this condition as indicating that it cannot be determined, from this condition alone, whether said algae is most likely in said growth stage g0.

11. The method of claim 9, further comprising choosing at least one of said error value ε(g) to be expressed as $$\varepsilon(g) = \sum_{n=1}^{N} w_n |\alpha(n; net) - \alpha(ref; n; \text{growth stage } g)|^p,$$

where g refers to said growth stage of said algae, α(n;net) is a light beam modification factor corresponding to said modified light beam intensity I(n), α(ref;n;growth stage g) is a reference light beam absorption factor corresponding to said reference light beam intensity I(ref;n;g) for said algae growth stage g, $w_n$ is a selected non-negative weight value, and p is a selected positive number.

12. The method of claim 9, further comprising choosing said ambient fluid to include at least one of air, a vacuum, fresh water and marine water.

13. The method of claim 9, further comprising:
providing an estimate LC(g') of lipid content in said algae at each of a sequence of growth stages g'=1, ..., G';
estimating a growth stage, g'=g'(max) at which the lipid content LC(g') is approximately maximized; and
when said most likely growth stage g0 has a value at least equal to g'(max), terminating a growth process for said algae.

14. The method of claim 9, further comprising:
providing an estimate LC of lipid content in said algae at each of a sequence of growth stages g', corresponding to times $t=t_{g'}$, (g'=1, ..., G'; G'≧3};
estimating a time rate of change, ∂LC/∂t, of the lipid content LC for at least one selected time, $t=t_{g''}$, $t=t_{g'+1}$ and $t=t_{g'+2}$; and
when the estimated time rate of change of the lipid content for the selected time, $t=t_{g''}$, is either negative or 0 or has a small positive value, terminating growth of said algae at a time contemporaneous with the time $t=t_{g''}$.

15. The method of claim 14, wherein said process of estimating said time rate of change aLuat comprises:
providing a sequence $\{LC(t_m)\}_m$ of measurements or estimates of lipid content of a selected alga at a sequence of times, $t=t_m$, and
for at least three measurement times, $t=t_{m-1}, t_m, t_{m+1}$, with $t_{m-1} < t_m < t_{m+1}$, estimating said lipid content growth rate at a time, $t=t_m$, as $$\{\partial Q/\partial t\}_{t=tm} = LC(t_{m-1})(t_m-t_{m+1})/(t_{m-1}-t_m)(t_{m-1}-t_{m+1}) + LC(t_m)(2t_m-t_{m-1}-t_{m+1})/(t_m-t_{m-1})(t_m-t_{m+1}) + LC(t_{m+1})(t-t_{m-1})/(t_m-t_{m-1})(t_{m+1}-t_m).$$ (5).

16. The method of claim 9, wherein said process of providing N reference light beam intensities I(ref;n;g) for at least one of said algae growth stages g for said selected algae comprises
providing an exponential absorption value α(ambient;n) for a thickness of said ambient fluid in which said algae is immersed;
providing an exponential absorption value α(window;n) for said chamber window or chamber windows through which at least one of said light beams passes;
estimating an overall light beam attenuation as exp{−α(algae;n;g)}, and
estimating said reference light beam intensity by a relation I(net;n;g)=$I_0$(n) exp{α(ambient;n)+α(window;n)} exp{−α(algae;n)}.

* * * * *